(12) United States Patent
Bretschneider et al.

(10) Patent No.: US 9,480,253 B2
(45) Date of Patent: Nov. 1, 2016

(54) USE OF 3-(2,4,6-TRIMETHYLPHENYL)-4-NEOPENTYLCARBONYLOXY-5,5-TETRAMETHYLENE-DELTA-3-DIHYDROFURAN-2-ONE FOR CONTROLLING PSYLLIDS

(75) Inventors: Thomas Bretschneider, Lohmar (DE); Reiner Fischer, Monheim (DE); Ernst Brück, Bergisch Gladbach (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 2384 days.

(21) Appl. No.: 11/631,650

(22) PCT Filed: Jun. 23, 2005

(86) PCT No.: PCT/EP2005/006780
§ 371 (c)(1),
(2), (4) Date: Jun. 18, 2007

(87) PCT Pub. No.: WO2006/002824
PCT Pub. Date: Jan. 12, 2006

(65) Prior Publication Data
US 2007/0254949 A1 Nov. 1, 2007

(30) Foreign Application Priority Data
Jul. 5, 2004 (DE) .......... 10 2004 032 420

(51) Int. Cl.
*A01N 43/12* (2006.01)
(52) U.S. Cl.
CPC .................. *A01N 43/12* (2013.01)
(58) Field of Classification Search
CPC .................................... A01N 43/12
See application file for complete search history.

(56) References Cited

U.S. PATENT DOCUMENTS

| | | | |
|---|---|---|---|
| 5,262,383 A | 11/1993 | Fischer et al. | |
| 5,877,012 A * | 3/1999 | Estruch et al. | 435/252.3 |
| 6,436,988 B1 | 8/2002 | Wachendorff-Neumann | |
| 6,716,874 B1 * | 4/2004 | Bretschneider et al. | 514/461 |
| 6,894,074 B2 * | 5/2005 | Bretschneider et al. | 514/462 |
| 2002/0169329 A1 * | 11/2002 | Mori et al. | 548/317.1 |

FOREIGN PATENT DOCUMENTS

| | | |
|---|---|---|
| EP | 0 528 156 A1 | 2/1993 |
| WO | WO 00/42850 A1 | 7/2000 |

OTHER PUBLICATIONS

Potatoes, USDA Economic Research Service article accessed via http://www.ers.usda.gov/topics/crops/vegetables-pulses/potatoes.aspx#.U7Vx3vIdWI8 on Jul. 3, 2014 Last updated: Tuesday, Oct. 9, 2012, pp. 1-4.*
De Maeyer, L., et al., "Spirodiclofen: a broad-spectrum acaricide with insecticidal properties: efficacy on *Psylla pyri* and scales *Lepidosaphes ulmi* and *Quadraspidiotus perniciosus*," *The BCPC Conference-Pests & Diseases 2002*, pp. 65-72, BCPC (2002).
International Search Report for International Application No. PCT/EP2005/006780, European Patent Office, Netherlands, mailed on Nov. 24, 2005.

* cited by examiner

*Primary Examiner* — Kortney L Klinkel
(74) *Attorney, Agent, or Firm* — Sterne, Kessler, Goldstein & Fox P.L.L.C.

(57) ABSTRACT

The present application relates to the use of 3-(2,4,6-trimethylphenyl)-4-neopentyl-carbonyloxy-5,5-tetramethylene-$\Delta^3$-dihydrofuran-2-one for controlling insects from the family Psyllidae (psyllids).

21 Claims, No Drawings

USE OF 3-(2,4,6-TRIMETHYLPHENYL)-4-NEOPENTYLCARBONYLOXY-5,5-TETRAMETHYLENE-DELTA-3-DIHYDROFURAN-2-ONE FOR CONTROLLING PSYLLIDS

The present application relates to the use of 3-(2,4,6-trimethylphenyl)-4-neopentyl-carbonyloxy-5,5-tetramethylene-$\Delta^3$-dihydrofuran-2-one for controlling insects from the family Psyllidae (psyllids).

The compound 3-(2,4,6-trimethylphenyl)-4-neopentyl-carbonyloxy-5,5-tetramethylene-$\Delta^3$-dihydrofuran-2-one is known from EP-A-0 528 156.

It is furthermore known that spirodiclofen has an ovicidal activity against psyllids under certain conditions. However, the timing of application is very limited (De Maeyer et al.; BCPC-Conference (2002), Vol. 1, 65-72).

Furthermore, it is known from EP-A-0 528 156 that 3-(2,4,6-trimethylphenyl)-4-neopentyl-carbonyloxy-5,5-tetramethylene-$\Delta^3$-dihydrofuran-2-one has an acaricidal activity and is active against insects from the family Aleyrodidae.

Surprisingly, it has now been found that 3-(2,4,6-trimethylphenyl)-4-neopentylcarbonyloxy-5,5-tetramethylene-$\Delta^3$-dihydrofuran-2-one is particularly suitable for controlling insects from the family Psyllidae and, moreover, is considerably more effective than spirodiclofen.

Accordingly, the present invention relates to the use of 3-(2,4,6-trimethylphenyl)-4-neopentylcarbonyloxy-5,5-tetramethylene-$\Delta^3$-dihydrofuran-2-one for controlling insects from the family Psyllidae.

3-(2,4,6-Trimethylphenyl)-4-neopentylcarbonyloxy-5,5-tetramethylene-$\Delta^3$-dihydrofuran-2-one has the formula (I):

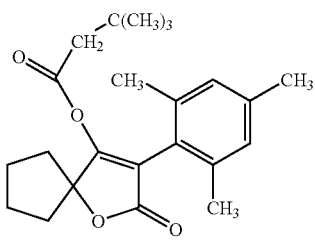

The compound of the formula (I) can preferably be used for controlling insects from the genera *Psylla, Diaphorina, Trioza, Paratrioza, Tenalaphara, Agonoscena*. Examples which may be mentioned are the following species: *Psylla costalis, Psylla pyricola, Psylla pyrisuga, Psylla mali, Psylla piri, Diaphorina citri, Trioza erythrea, Paratrioza cockerelli, Tenalaphara malayensis* (old)=*Allocarsidara malayensis* (new).

In principle, the compound of formula (I) can be employed in a multiplicity of crops, preferably pome fruit (for example apples, pears), vegetables (for example tomatoes, chillis, aubergines, carrots, beans, peppers), potatoes, ornamentals, citrus fruit (for example oranges, grapefruits, tangerines), tropical crops such as, for example, durian, stone fruit (for example cherries, plums, quetsch), nuts (for example pistachios).

All plants and plant parts can be treated in accordance with the invention. In this context, plants are understood as meaning all plants and plant populations such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties which are capable or not capable of being protected by Plant Breeders' Rights. Plant parts are understood as meaning all aerial and subterranean parts and organs of the plants such as shoot, leaf, flower and root, examples which may be mentioned being leaves, needles, stalks, stems, flowers, fruit bodies, fruits and seeds, but also roots, tubers and rhizomes. The plant parts also include crop material and vegetative and generative propagation material, for example cuttings, tubers, rhizomes, slips and seeds.

The treatment according to the invention with the active compound, of the plants and plant parts, is effected directly or by treating their environment, habitat or store using conventional treatment methods, for example by dipping, spraying, fumigating, fogging, scattering, brushing on, injecting, and, in the case of propagation material, in particular seeds, furthermore by coating with one or more coats.

As already mentioned above, all plants and their parts can be treated in accordance with the invention. In a preferred embodiment, plant species and plant varieties which are found in the wild or which are obtained by traditional biological breeding methods, such as hybridization or protoplast fusion, and parts of these species and varieties are treated. In a further preferred embodiment, transgenic plants and plant varieties which have been obtained by recombinant methods, if appropriate in combination with traditional methods (genetically modified organisms) and their parts are treated. The term "parts", "parts of plants" or "plant parts" have been described above.

Plants which are especially preferably treated in accordance with the invention are those of the varieties which are in each case commercially available or in use. Plant varieties are understood as meaning plants with novel traits which have been bred both by conventional breeding, by mutagenesis or by recombinant DNA techniques. They may take the form of varieties, biotypes or genotypes.

Depending on the plant species or plant varieties, their location and growth conditions (soils, climate, vegetation period, nutrition), superadditive ("synergistic") effects may also occur as a result of the treatment according to the invention. Effects which exceed the effects actually to be expected are, for example, reduced application rates and/or widened activity spectrum and/or an enhancement of the activity of the substances and compositions which can be used in accordance with the invention, better plant growth, increased tolerance to high or low temperatures, increased tolerance to drought or to water or soil salinity, increased flowering performance, facilitated harvest, speedier maturation, higher yields, higher quality and/or higher nutritional value of the crop products, better storability and/or processability of the crop products.

The preferred transgenic plants or plant varieties (plants or plant varieties obtained by means of genetic engineering) which are to be treated in accordance with the invention include all plants which, by means of the recombinant modification, have received genetic material which confers particularly advantageous valuable traits to these plants. Examples of such traits are better plant growth, increased tolerance to high or low temperatures, increased tolerance to drought or to water or soil salinity, increased flowering performance, facilitated harvest, speedier maturation, higher yields, higher quality and/or higher nutritional value of the crop products, better storability and/or processability of the crop products. Other examples of such traits which are particularly emphasized are an improved defence of the plants against animal and microbial pests such as insects, mites, phytopathogenic fungi bacteria and/or viruses, and an increased tolerance of the plants to specific herbicidal active compounds. Examples of transgenic plants which are mentioned are the important crop plants such as cereals (wheat, rice), maize, soybean, potato, cotton, tobacco, oilseed rape and fruit plants (with the fruits apples, pears, citrus fruits and grapes), with particular emphasis on maize, soybean, potatoes, cotton, tobacco and oilseed rape. Traits which are particularly emphasized are the increased defence of the plants against insects, arachnids, nematodes and slugs and snails as the result of toxins formed in the plants, in particular toxins which are produced in the plants by the genetic material of *Bacillus Thuringiensis* (for example by the genes CryIA(a), CryIA(b), CryIA(c), CryIIA, CryIIIA, CryIIIB2, Cry9c, Cry2Ab, Cry3Bb and CryIF and their combinations) (hereinbelow "Bt plants"). Traits which are also particularly emphasized are the increased defence of plants against fungi bacteria and viruses by systemic acquired resistance (SAR), systemin, phytoalexins, elicitors and resistance genes and correspondingly expressed proteins and toxins. Traits which are furthermore especially emphasized are the increased tolerance of the plants to specific herbicidal active compounds, for example imidazolinones, sulphonylureas, glyphosate or phosphinothricin (for example "PAT" gene). The specific genes which confer the desired traits can also occur in combinations with one another in the transgenic plants. Examples of "Bt plants" which may be mentioned are maize varieties, cotton varieties, soybean varieties and potato varieties sold under the trade names YIELD GARD® (for example maize, cotton, soybean), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (glyphosate tolerance, for example maize, cotton, soybean), Liberty Link® (phosphinothricin tolerance, for example oilseed rape), IMI® (imidazolinone tolerance) and STS® (sulphonylurea tolerance, for example maize). Herbicide-resistant plants (bred conventionally for herbicide tolerance) which may also be mentioned are the varieties sold under the name Clearfield® (for example maize). Naturally, what has been said also applies to plant varieties which will be developed, or marketed, in the future and which have these genetic traits or traits to be developed in the future.

The active compound of the formula (I) can be converted into the customary formulations, such as solutions, emulsions, wettable powders, suspensions, powders, dusts, pastes, soluble powders, granules, suspoemulsion concentrates, natural and synthetic materials impregnated with active compound, and ultrafine encapsulations in polymeric materials.

These formulations are produced in the known manner, for example by mixing the active compound with extenders, that is, liquid solvents and/or solid carriers, optionally with the use of surfactants, that is, emulsifiers and/or dispersants and/or foam formers.

In the case of the use of water as an extender, organic solvents can, for example, also be used as cosolvents. Liquid solvents which are suitable are mainly: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral oils and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and water.

Solid carriers which are suitable are:

for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%, and additionally preferably extenders and/or surfactants.

The active compound content of the use forms prepared from the commercially available formulations can vary within wide ranges. The active compound concentration of the use forms can be in the range of from 0.0000001 up to 95% by weight of active compound, preferably between 0.0001 and 1% by weight.

Application is in a customary manner which is appropriate for the use forms.

Preparation of the Compound of the Formula (I):

5.45 g (20 mmol) of 3-(2,4,6-trimethylphenyl)-4-hydroxy-5,5-tetramethylene-$\Delta^3$-dihydrofuran-2-one (disclosed in EP-A-0 528 156) are introduced into 80 ml of dichloromethane, 3.04 g (30 mmol) of triethylamine are added, and a solution of 3.50 g (26 mmol) of 3,3-dimethylbutyryl chloride in 20 ml of dichloromethane is subsequently added dropwise at 0-10° C.

After 2 hours, a further 0.50 g (5 mmol) of triethylamine and 0.40 g (3 mmol) of acid chloride are added and the mixture is stirred for a further 16 hours at room temperature.

For work-up, the mixture is washed twice with 10% strength citric acid and twice with 1N sodium hydroxide solution, and the organic phase is dried with sodium sulphate and concentrated.

The crude product is purified further by trituration with petroleum ether, filtration under suction and drying.

Yield: 4.50 g of white solid (61% of theory) of melting point 98° C.

USE EXAMPLE

Example A

Pest: *Trioza erythreae*
Plant: Orange

The compound of the formula (I) (240 SC) was tested at an application rate of 144 g a.i./ha+0.2% a.i. rapeseed oil methyl ester (RME) at 540 l water per ha in comparison with spirodiclofen application rate comparison.

Spraying was effected by means of a pneumatic knapsack sprayer.

The experiment was carried out using one tree per plot and three replications. In each case two applications were carried out at an interval of one week.

The activity against psyllids was determined by counting the number of live animals on 20 leaves per tree 7 days after the first treatment and 7 and 13 days after the last treatment. The efficacy was calculated with the aid of Abbott's formula.

| Compound | Application rate g/ha | Efficacy in % Abbott | | |
|---|---|---|---|---|
| | | 7TNAA | 7TNAB | 13TNAB |
| Compound of the formula (I) 240 SC + 0.2% RME | 144 | 95 | 97.5 | 95.2 |
| Spirodiclofen 240 SC + 0.2% RME | 144 | 80.3 | 91.5 | 88.1 |

Example B

Pest: *Paratrioza cockerelli*
Plant: Tomato

The compound of the formula (I) (240 SC) was tested at an application rate of 72 g a.i./ha at a water application rate of 345 l ha in comparison with Leverage (48 g a.i./ha imidacloprid+33 g a.i./ha cyfluthrin).

Spraying was effected by means of a manually operated knapsack sprayer.

The experiment was carried out with 10-m² plots and three replications. In each case two applications were carried out at an interval of one week.

The activity against psyllids was determined by counting the number of live animals on 10 leaves 7 days after the first treatment and 7 and 14 days after the second treatment. The efficacy was calculated with the aid of Abbott's formula.

| Compound | Application rate g/ha | Efficacy in % Abbott | | |
|---|---|---|---|---|
| | | 7TNAA | 7TNAB | 14TNAB |
| Compound of the formula (I) 240 SC | 72 | 80.3 | 84.8 | 98.7 |
| Leverage imidacloprid + cyfluthrin | 48 + 33 | 75.4 | 81.1 | 92.1 |

The invention claimed is:

1. A method for killing an insect selected from the group consisting of *Psylla costalis, Psylla pyricola, Psylla pyrisuga, Psylla mali, Psylla pini, Diaphorina citri, Trioza erythrea, Paratrioza cockerelli,* and *Allocarsidara malayensis* comprising applying to said insect or an environment or a habitat thereof a compound of formula (I)

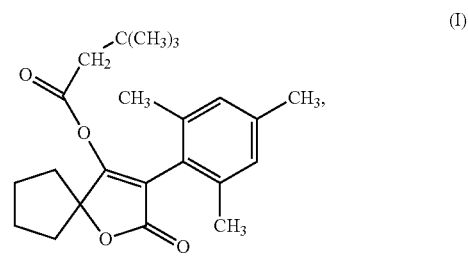 [SMILES: Cc1cc(C)c(C2=C(OC(=O)CC(C)(C)C)C3(CCCC3)OC2=O)c(C)c1]

as the sole insecticide and optionally a carrier and/or surfactant.

2. The method according to claim 1 comprising applying the compound of formula (I) to the environment or the habitat.

3. The method according to claim 2 wherein the environment or the habitat is a crop.

4. The method according to claim 3 wherein the crop is pome fruit, vegetables, potatoes, ornamentals, citrus fruit, a tropical crop, or nuts.

5. The method according to claim 1 wherein the insect is *Psylla costalis*.

6. The method according to claim 1 wherein the insect is *Psylla pyricola*.

7. The method according to claim 1 wherein the insect is *Psylla pyrisuga*.

8. The method according to claim 1 wherein the insect is *Psylla mali*.

9. The method according to claim 1 wherein the insect is *Psylla piri*.

10. the method according to claim 1 wherein the insect is *Diaphonina citri*.

11. The method according to claim 1 wherein the insect is *Trioza erythrea*.

12. The method according to claim 1 wherein the insect is *Paratrioza cockerelli*.

13. The method according to claim 1 wherein the insect is *Allocarsidara malayensis*.

14. The method according to claim 4 wherein the crop is pome fruit.

15. The method according to claim 4 wherein the crop is vegetables.

16. The method according to claim 4 wherein the crop is potatoes.

17. The method according to claim 4 wherein the crop is ornamentals.

18. The method according to claim 4 wherein the crop is citrus fruit.

19. The method according to claim 4 wherein the crop is a tropical crop.

20. The method according to claim 4 wherein the crop is nuts.

21. A method for killing an insect selected from the group consisting of *Psylla costalis, Psylla pyricola, Psylla pyrisuga, Psylla mila, Psylla piri, Diaphorina citri, Trioza euthrea, Paratnioza cockerelli,* and *Ailocarsidara malayen-* sis comprising contacting a plant or one or more plant parts in need of said killing with an effective amount of a compound of formula (I)
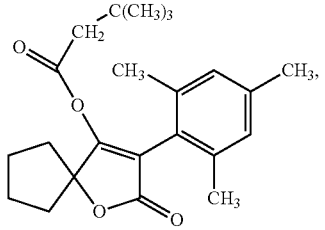
as the sole insecticide and optionally a carrier and/or surfactant.
* * * * *